United States Patent [19]

Otake et al.

[11] Patent Number: 4,731,454

[45] Date of Patent: Mar. 15, 1988

[54] PROCESS FOR PRODUCING LACTAMS

[75] Inventors: Masayuki Otake; Isamu Fukushima, both of Kurashiki, Japan

[73] Assignee: Mitsubishi Chemical Industries Limited, Tokyo, Japan

[21] Appl. No.: 55,380

[22] Filed: May 29, 1987

[30] Foreign Application Priority Data

Jun. 9, 1986 [JP] Japan .................................. 51-133031
Jul. 18, 1986 [JP] Japan .................................. 51-169493

[51] Int. Cl.⁴ ........................................... C07D 207/12
[52] U.S. Cl. .................................... 548/543; 540/532; 546/243; 548/544; 548/552
[58] Field of Search ........................ 548/543, 544, 552; 546/243; 540/532

[56] References Cited

U.S. PATENT DOCUMENTS 3,109,005 10/1963 Lidov .................................. 548/554
3,681,387 8/1972 Hollstein et al. ..................... 548/552
3,745,164 7/1973 Adamek ............................... 546/243

Primary Examiner—Richard A. Schwartz
Attorney, Agent, or Firm—Oblon, Fisher, Spivak, McClelland & Maier

[57] ABSTRACT

A method for producing a lactam having the formula:

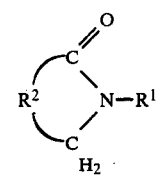

wherein $R^1$ is a hydrogen atom, or a straight chain or branched chain alkyl group having from 1 to 5 carbon atoms, and $R^2$ is an organic group having at least 2 carbon atoms, and connected at both ends to the cyclic acid imide group, which comprises reducing a cyclic acid imide having the formula:

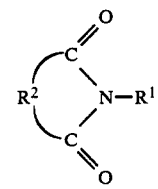

wherein $R^1$ and $R^2$ are as defined above, or its precursor, with hydrogen by means of a cobalt-based catalyst comprising (a) cobalt and (b) at least one modifier component selected from the group consisting of molybdenum, tungsten and rhenium.

7 Claims, No Drawings

PROCESS FOR PRODUCING LACTAMS

BACKGROUND OF THE INVENTION

1. FIELD OF THE INVENTION

The present invention relates to a method for producing a lactam having the formula:

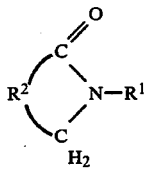
(I)

wherein $R^1$ is a hydrogen atom, or a straight chain or branched chain alkyl group having from 1 to 5 carbon atoms, and $R^2$ is an organic group having at least 2 carbon atoms, and connected at both ends to the cyclic acid imide group, which comprises reducing a cyclic acid imide having the formula:

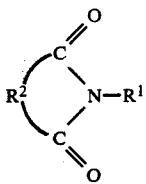
(II)

wherein $R^1$ and $R^2$ are as defined above, or its precursor, with hydrogen. More particularly, it relates to a catalyst having excellent performance for the reaction.

DISCUSSION OF THE INVENTION

Lactams are generally useful as starting materials for organic synthesis, and they are also used as starting materials for the synthesis of polymers by ring-opening polymerization. Further, they have various applications as stable polar solvents. As a typical example, N-methylpyrrolidone is useful as a solvent for a polymer substance such as an acrylonitrile polymer, a polyurethane, a polyimide, a polyamide, a polyarylene sulfide or a polyarylene oxide, as a solvent for extraction of acetylene, butadiene or an aromatic hydrocarbon, and as a solvent for various medicines or for organic chemical reactions. A number of methods have been proposed for the production of lactams. For the production of a lactam having a large number of ring-constituting members, a method is known which involves Beckmann rearrangement of an oxime or photo-induced nitroso conversion of a cycloolefin. Whereas, for the production of a lactam having a small number of ring-constituting members, it has been common to employ a method wherein such a lactam is prepared by the reaction of a lactone and an amine. However, such a method is not necessarily advantageous since lactone itself is expensive. Studies on some other methods have been also reported. For instance, with respect to a 2-pyrrolidone as a 5-membered lactam, a method has been proposed wherein a $C_1$-material such as carbon monooxide or hydrogen cyanide is added to a $C_3$-material such as acrylonitrile, acrylamide, acrylate, allyl alcohol or its ester, followed by hydrolysis and reduction by hydrogenation. However, this method is not necessarily advantageous, since the process steps are complicated, and a high temperature and a high pressure are required.

With respect to the above-mentioned 5-membered lactam, a method is known wherein a 2-pyrrolidone is synthesized by the reduction of a succinic acid imide. For example, V. I. Romanovskii et al (Khim. Prom., 1963(7), 491-2) reported that an N-methylsuccinic acid imide was prepared from succinic acid and methylamine via a monoamide, and it was then reduced with hydrogen at a temperature of from 200° to 215° C. under a pressure of from 200 to 220 atm for from 4 to 5 hours by means of a Raney nickel catalyst, whereby N-methyl-2-pyrrolidone was obtained in a yield of 71.6%. In U.S. Pat. No. 3,109,005, it is disclosed that a yield of from 65 to 76% has been attained by the reaction at a temperature of from 150° to 350° C. under a pressure of from 100 to 300 atm for from 10 to 12 hours in the presence of a Raney nickel or Raney cobalt, or a hydrogenation catalyst such as palladium or platinum. In Japanese unexamined patent publication No. 16,451/1972, it is disclosed that an alkylamine and an acid selected from the group consisting of maleic acid, fumaric acid and succinic acid, are hydrogenated in an aqueous solution system in the presence of a palladium catalyst to obtain N-methyl-2-pyrrolidone in a yield of 44%. However, according to these conventional methods, a high temperature and a high pressure are required, and the reaction time is requied to be rather long, whereby a large size reactor will be required to carry out them on an industrial scale. Further, the yield of N-methyl-2-pyrrolidone is still inadequate.

SUMMARY OF THE INVENTION

It is an object of the present invention to provide a method whereby a lactam such as N-methyl-2-pyrrolidone can be produced advantageously on an industrial scale. More specifically, it is an object of the present invention to provide a catalyst having improved activity and selectivity to convert a cyclic acid imide or its precursor to the corresponding lactam under a mild condition.

Under the above-mentioned circumstances, the present inventors have conducted extensive research, and as a result, have found that a lactam can be obtained in good yield by using a catalyst comprising (a) cobalt and (b) at least one modifier component selected from the group consisting of molybdenum, tungsten and rhenium in the reduction of a cyclic acid imide or its precursor with hydrogen to obtain the corresponding lactam.

The present invention provides a method for producing a lactam having the formula:

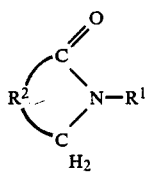
(I)

wherein $R^1$ is a hydrogen atom, or a straight chain or branched chain alkyl group having from 1 to 5 carbon atoms, and $R^2$ is an organic group having at least 2 carbon atoms, and connected at both ends to the cyclic acid imide group, which comprises reducing a cyclic acid imide having the formula:

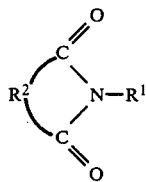

(II)

wherein R[1] and R[2] are as defined above, or its precursor, with hydrogen by means of a cobalt-based catalyst comprising (a) cobalt and (b) at least one modifier component selected from the group consisting of molybdenum, tungsten and rhenium.

DETAILED DESCRIPTION OF THE PREFERRED EMBODIMENTS

Now, the present invention will be described in detail with reference to the preferred embodiments.

The cyclic acid imide used as a starting material in the present invention, is represented by the formula:

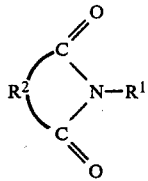

(II)

In the above formula, R[1] is a hydrogen atom or a straight chain or branched chain alkyl group having from 1 to 5 carbon atoms. More specifically, it includes hydyrogen, methyl, ethyl, propyl, isopropyl, butyl, sec-butyl, isobutyl, tert-butyl, amyl, isoamyl and neopentyl. Further, a part of the alkyl group may be substituted by a halogen atom or a hydroxyl group. The present invention may be applicable to a case where R[1] is an organic group having at least 5 carbon atoms, such as cyclohexyl, phenyl or tolyl. However, the application of such compounds is presently very limited.

R[2] is an organic group having at least two carbon atoms and connected at both ends to the cyclic acid imide group to form a dibasic acid. Typical examples of such a dibasic acid are maleic acid, succinic acid, fumaric acid, malic acid, chloromaleic acid, glutaric acid and adipic acid. Further, the present invention is applicable also to an aromatic dicarboxylic acid such as phthalic acid, or a dicarboxylic acid such as tetrahydrophthalic acid or 1,2-cyclohexane dicarboxylic acid. An olefin bond will be hydrogenated simultaneously, and therefore, a saturated lactam will be obtained even if an unsaturated dibasic acid imide is used as the starting material. In the present invention, a precursor of an acid imide may be used as the starting material. Such a precursor includes all kinds of compounds which are capable of forming acid imides in the reaction system or by a reaction in a preliminary stage such as heating for dehydration, hydrolysis or decomposition for hydrogenation. Compounds represented by the following formulas are preferred.

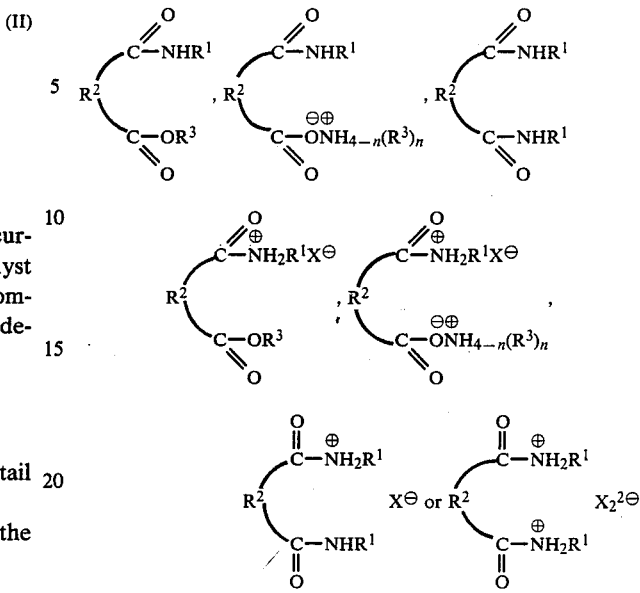

wherein R[1] and R[2] are as defined in claim 1, R[3] is a hydrogen atom, a straight chain or branched chain alkyl group having from 1 to 5 carbon atoms, or an aryl group, X is a mineral acid anion, and n is an integer of from 1 to 3.

More preferably, a dibasic acid monoamide derivative is advantageous. As such a derivative, a maleamic acid or succinic acid monoamide derivative may be mentioned. These compounds can readily be dehydrated and converted into imides simply by heating under no catalytic condition, and can be supplied to the subsequent hydrogenation step after or without separating water. However, it is preferred to preliminarily remove the water.

The catalyst used in the present invention is an improved cobalt-based catalyst. By the combination of (a) cobalt with (b) at least one modifier component selected from the group consisting of molybdenum, tungsten and rhenium, the catalytic activity and selectivity have been remarkably improved. There is no particular restriction as to the proportions of the cobalt (a) and the modifier component (b). However, the atomic ratio of the modifier component (b) to the cobalt (a) in the catalyst is preferably within a range of from 0.001 to 1.0. More specifically, when the modifier is molybdenum or tungsten, the atomic ratio is preferably from 0.001 to 1.0, more preferably from 0.005 to 0.1. Likewise, in the case of rhenium, the atomic ratio is preferably from 0.001 to 0.5, more preferably from 0.01 to 0.2. When two or more modifier components are used in combination, the atomic ratio is preferably selected within the above range.

As the starting material of cobalt used for the catalyst, a cobalt salt of a mineral acid such as nitric acid, sulfuric acid or hydrochloric acid, or of an organic acid such as formic acid, acetic acid or lactic acid, or a carbonate, an oxide or various complex salts such as an amine complex, may be employed. However, in the case of a soluble salt, it is preferred that an aqueous solution of ammonium molybdate, an alkali metal carbonate, ammonium carbonate or ammonium hydrogencarbonate, is added thereto to precipitate its molybdate, carbonate or basic carbonate, which is then taken out, or impregnated and supported on a carrier.

As the carrier, various materials may be employed which do not adversely affect industrially applicable reactions. For example, silica, silica alumina, alumina, diatomaceous earth, zirconia, aluminum phosphate, magnesia and active carbon may be used in a powder form or in a shaped product form.

As the molybdenum source, sodium molybdate, ammonium paramolybdate, and an oxyacid such as 12-molybdophosphoric acid, a polyacid and salts thereof, may commonly be used.

As the tungsten source, sodium tungstate, ammonium paratungstate, and an oxyacid such as 12-tungstophosphoric acid, a polyacid and salts thereof, may be used.

As the rhenium source, various compounds capable of forming rhenium metal by oxidation, may be employed. It is usual to employ rhenium heptoxide or ammonium perrhenate.

For the production of the catalyst, common conventional methods may be employed including various steps such as mixing, drying and reducing the starting materials. For instance, aqueous solutions of cobalt nitrate and ammonium carbonate containing or not containing a carrier, are prepared, respectively, and then mixed. The pH of the mixture is adjusted to precipitate basic cobalt carbonate, which is then washed, and after an addition of an aqueous ammonium molybdate solution, an aqueous ammonium tungstate solution or an aqueous rhenium heptoxide solution, thoroughly kneaded, then dried (80°–120° C.) and heated and finally reduced at a temperature of from 400° to 500° C., to obtain a catalyst.

The reaction is conducted by reacting a solution containing the cyclic acid imide or its precursor as the starting material and the catalyst, with hydrogen at an elevated temperature and pressure. As the solvent, it is advantageous to use the reaction product lactam with a view to rationalization of the subsequent purification step. Otherwise, a low-boiling or high-boiling common solvent such as dioxane, N-methyl-2-pyrrolidone, tetrahydofuran, a diethylene glycol dialkyl ether or liquid paraffin, may be used. The reaction temperature is usually from 160° to 300° C., preferably from 200° to 270° C. The pressure may usually be within a range of from 10 to 300 kg/cm$^2$G, preferably from 20 to 150 kg/cm$^2$G. The most practical operational pressure is from 20 to 50 kg/cm$^2$G. The reaction may be conducted by either a batch system or a continuous system. As a method for effectively separating the product from the catalyst, a system may be mentioned wherein hydrogen is circulated in the reaction system so that the reaction product lactam and water are withdrawn together with hydrogen. This system is particularly advantageously employed for the production of a low-boiling lactam such as an N-alkyl-2-pyrrolidone.

Further, in the present invention, the selectivity can further be improved by adding an acidic substance to the reduction reaction system, whereby the side reaction for producing a gasification product such as a lower hydrocarbon such as methane can be prevented.

As such an acidic substance, various inorganic acids may be mentioned including a mineral acid such as phosphoric acid, nitric acid, sulfuric acid, hydrochloric acid, phosphorus acid or pyrophosphoric acid, an isopolyacid or heteropolyphosphoric acid such as condensed phosphoric acid, molybdic acid, tungstophosphoric acid, molybdophosphoric acid, tungstomolybdophosphoric acid or molybdovanadophosphoric acid, and a heteropolysilicic acid such as tungstosilicic acid, molybdosilicic acid or tungstomolybdosilicic acid. If desired, it is possible to employ a salt which is capable of forming such a acidic substance by hydrolysis to provide acidity. In the present invention, it is possible to use an organic carboxylic acid such as acetic acid, propionic acid, butyric acid, succinic acid, lactic acid, malic acid or oxalic acid, an aromatic sulfonic acid such as p-toluene sulfonic acid, or an acid such as sulfosuccinic acid. Further, trichloroacetic acid, trifluoroacetic acid and trifluoromethane sulfonic acid may also be employed. However, these acids as well as inorganic halogen-containing compounds may create a problem of corrosion.

The addition of such an acidic substance is limited because it affects the activity of the catalyst for the hydrogenation reduction. It is incorporated usually within a range of from 10 to 5,000 ppm, preferably from 50 to 300 ppm, relative to the amount (by weight) of the liquid in the reaction system. The manner of incorporation varies depending upon the reaction system. Namely, it may be incorporated preliminarily to the reaction tank, or it may be continuously introduced into the reaction tank to supplement the evaporation loss. Now, the present invention will be described in further detail with reference to Examples. However, it should be understood that the present invention is by no means restricted to such specific Examples.

EXAMPLE 1

An aqueous solution prepared by dissolving 24 g of ammonium hydrogencarbonate in 150 g of distilled water, was dropwise added under stirring to an aqueous solution prepared by dissolving 30 g of cobalt nitrate [Co(NO$_3$)$_2$.6H$_2$O] in 24 g of distilled water. The formed precipitates of basic cobalt carbonate were collected by filtration. The cake was washed three times with 400 cc of distilled water. To this cake, an aqueous solution prepared by dissolving 0.73 g of rhenium heptoxide [Re$_2$O$_7$] and 0.27 g of ammonium molybdate [(NH$_4$)$_6$Mo$_7$O$_{24}$.4H$_2$O] in 15 g of distilled water, was added, and the mixture was kneaded for 1 hour, and then dried at a temperature of from 80° to 120° C. for about 6 hours.

The powder thus obtained, was heated to 200° C. over a period of about 30 minutes in a nitrogen stream at a flow rate of 50 cc/min., and then heated to 450° C. over a period of about 1 hour while gradually introducing hydrogen. When the temperature reached 450° C., the atmosphere was changed to a stream of pure hydrogen, and reduction was conducted at a flow rate of hydrogen of 30 cc/min. for 3 hours. After the completion of the reduction, the powder was cooled to 200° C., and the stream was switched to a nitrogen stream, and the mixture was cooled to room temperature and kept under a sealed condition.

The reaction was conducted in such a manner that under a nitrogen atmosphere, 1.75 g of the catalyst thus obtained and 20 g of succinic acid N-methylimide and 30 g of dioxane were charged in a top and bottom stirring type autoclave having a capacity of 100 ml, and after substituting hydrogen gas for the nitrogen atmosphere, contacted and reacted with hydrogen under a reaction pressure of 50 kg/cm$^2$G at a reaction temperature of 230° C. for 3 hours.

After the completion of the reaction, the reaction solution and gas were sampled, and subjected to a gas chromatography analysis. The results are shown in Table 1.

EXAMPLE 2

The reaction was conducted under the same condition as in Example 1 by using the same catalyst as obtained in Example 1 except that the amount of ammonium molybdate was changed so that the atomic ratio of molybdenum to cobalt (Mo/Co) became 0.03. The results of the reaction are shown in Table 1.

EXAMPLES 3 and 4

The reactions were conducted under the same condition as in Example 2 except that the catalyst was prepared by changing the amount of rhenium heptoxide so that the atomic ratio of rhenium to cobalt Re/Co became 0.06 and 0.10, respectively, and the reaction time was changed to one hour. The results thereby obtained are shown in Table 1.

EXAMPLE 5

The reaction was conducted in the same manner as in Example 1 by using a catalyst prepared in the same manner as in Example 1 except that no ammonium molybdate was added and the amount of rhenium heptoxide was changed so that the atomic ratio of rhenium to cobalt (Re/Co) became 0.03. The results are shown in Table 1.

EXAMPLES 6 to 8

The reactions were conducted in the same manner as in Example 1 by using a catalyst obtained in the same manner as in Example 1 except that no rhenium heptoxide was added and the amount of ammonium molybdate was changed so that the atomic ratio of molybdenum to cobalt (Mo/Co) became 0.015, 0.03 and 0.05, respectively. The results are shown in Table 1.

EXAMPLE 9

20 g of succinic acid N-methylamide and 30 g of N-methylpyrrolidone were charged into an autoclave, and after substituting nitrogen gas, the temperature was raised to 180° C. and maintained at that level for 2 hours while distilling off formed water. After cooling the reaction solution to room temperature, 1.75 g of the catalyst as used in Example 3 was charged to the reaction solution under a nitrogen atmosphere. After substituting hydrogen gas for the nitrogen atmosphere, the reaction was conducted under the same reaction condition as in Example 3. The results are shown in Table 1.

COMPARATIVE EXAMPLE 1

The catalyst was prepared in the same manner as in Example 1 except that neither rhenium nor molybdenum was added, and the reaction was conducted in the same manner as in Example 1. The results are shown in Table 1.

COMPARATIVE EXAMPLE 2

A catalyst was prepared in the same manner as in Example 1 except that an aqueous palladium nitrate solution was added to the basic cobalt carbonate cake, whereby the atomic ratio of palladium to cobalt (Pd/Co) was 0.03. By using this catalyst, the reaction was conducted under the same reaction condition as in Example 1. The results are shown in Table 2.

COMPARATIVE EXAMPLE 3

A catalyst was prepared in the same manner as in Example 1 except that a rhodium acetate solution was added to the basic cobalt carbonate cake so that the atomic ratio of rhodium to cobalt (Rh/Co) became 0.03. By using this catalyst, the reaction was conducted under the same reaction condition as in Example 1. The results are shown in Table 2.

TABLE 1

| Example No. | Catalyst composition | Re/Co atomic ratio | Mo/Co atomic ratio | Reaction time (hr) | Conversion (%) | N—methyl-2-pyrrolidone selectivity (%) |
|---|---|---|---|---|---|---|
| Example 1 | Co—Re—Mo | 0.03 | 0.015 | 3.0 | 85.59 | 90.42 |
| Example 2 | Co—Re—Mo | 0.03 | 0.03 | 3.0 | 68.75 | 91.34 |
| Example 3 | Co—Re—Mo | 0.06 | 0.03 | 1.0 | 66.91 | 91.16 |
| Example 4 | Co—Re—Mo | 0.10 | 0.03 | 1.0 | 78.58 | 91.74 |
| Example 5 | Co—Re | 0.03 | 0 | 3.0 | 63.96 | 89.29 |
| Example 6 | Co—Mo | 0 | 0.015 | 3.0 | 72.24 | 90.82 |
| Example 7 | Co—Mo | 0 | 0.03 | 3.0 | 64.73 | 90.54 |
| Example 8 | Co—Mo | 0 | 0.05 | 3.0 | 63.34 | 91.28 |
| Example 4 | Co—Re—Mo | 0.06 | 0.03 | 1.0 | 66.85 | 89.04 |
| Comparative Example 1 | Co | 0 | 0 | 3.0 | 34.18 | 77.53 |

TABLE 2

| Example No. | Catalyst composition | Rd/Co atomic ratio | Rh/Co atomic ratio | Reaction time (hr) | Conversion (%) | N—methyl-2-pyrrolidone selectivity (%) |
|---|---|---|---|---|---|---|
| Comparative Example 2 | Co—Pd | 0.03 | | 3.0 | 48.46 | 83.94 |
| Comparative Example 3 | Co—Rh | | 0.03 | 3.0 | 3.28 | 44.24 |

EXAMPLE 10

10 g of succinic acid imide and 40 g of dioxane were charged into a top and bottom stirring type autoclave, and by using 1.75 g of a catalyst prepared in the same manner as in Example 1 so that the atomic ratio of molybdenum to cobalt (Mo/Co) became 0.015 and the atomic ratio of rhenium to cobalt (Re/Co) became 0.06, the reaction was conducted under a hydrogen atmosphere under a pressure of 50 kg/cm$^2$G at 230° C. for 30 minutes. The reaction product was separated from the catalyst, and subjected to a gas chromatography analysis, whereby the conversion of succinic acid imide was found to be 75.73%, and the selectivity for 2-pyrrolidone was found to be 85.66%.

EXAMPLE 11

The reaction was conducted under the same reaction condition as in Example 1 by using a catalyst prepared in the same manner as in Example 1 except that ammonium methatungstate was added as tungsten instead of molybdenum so that the atomic ratio of tunsgten to cobalt (W/Co) became 0.015 and the atomic ratio of rhenium to cobalt (Re/Co) became 0.016. As a result, the conversion of N-methylsuccinic imide was 73.23%, and the selectivity for N-methylpyrrolidone was 91.41%.

EXAMPLE 12

To a basic cobalt carbonate cake prepared in the same manner as in Example 1, an aqueous solution prepared by dissolving 1.25 g of rhenium heptoxide and 0.27 g of ammonium molybdate [(NH$_4$)$_6$Mo$_7$O$_{24}$. 4H$_2$O] in 15 g of distilled water, was added, and the mixture was kneaded for 1 hour. Then, 6.0 g of zirconia was added thereto, and the mixture was further kneaded for 1 hour, and then dried at a temperature of from 80° to 120° C. The powder thus obtained was activated by reduction in the same manner as in Example 1. By using this catalyst, the reaction was conducted under the same reaction condition as in Example 3, and the reaction solution was analyzed, whereby the conversion of N-methylsuccinic acid imide was found to be 63.78%, and the selectivity for N-methylpyrrolidone was found to be 90.91%.

EXAMPLE 13

An aqueous solution prepared by dissolving 48 g of ammonium hydrogencarbonate (NH$_4$CHO$_3$) in 300 g of distilled water, was dropwise added under stirring to an aqueous solution prepared by dissolving 60 g of cobalt nitrate (Co(NO$_3$)$_2$.6H$_2$O) in 48 g of distilled water, and precipitates of basic cobalt carbonate formed, were collected by filtration. The cake thus obtained was washed three times with 400 cc of distilled water. To this cake, an aqueous solution prepared by dissolving 4.99 g of rhenium heptoxide (Re$_2$O$_7$) and 1.09 g of ammonium molybdenate [(NH$_4$)$_6$)Mo$_7$O$_{24}$.4H$_2$O] in 30 g of distilled water, was added, and the mixture was kneaded for 1 hour, and then dried at a temperature of from 80° to 120° C. for about 6 hours, (Re/Co=0.1, Mo/Co=0.03).

The powder thus obtained was heated to 200° C. over a period of about 30 minutes in a nitrogen stream at a flow rate of 50 cc/min., and then the temperature was raised to 450° C. over a period of about 1 hour while gradually supplying hydrogen. When the temperature reached 450° C., the stream was switched to a pure hydrogen stream of 30 cc/min., and reduction was conducted for 3 hours. Then, the reaction system was cooled to 200° C., and the stream was switched to a nitrogen stream. The powder was cooled to room temperature and stored in a sealed condition.

10 g of the catalyst thus obtained, 60 g of N-methylsuccinic acid imide, 140 g of N-methylpyrrolidone and 0.0411 g of phosphoric acid, were charged into an induction rotational stirring type autoclave having a capacity of 500 ml under a nitrogen atmosphere, and hydrogen gas was substituted for the nitrogen atmosphere. Then, a continuous reaction was conducted by continuously supplying an N-methylpyrrolidone solution containing 80% by weight of N-methylsuccinic acid imide and hydrogen into the autoclave under a reaction pressure of 35 kg/cm$^2$G and at a reaction temperature of 230° C., while the formed liquid was withdrawn together with hydrogen in the vapor phase. The amount of the feed starting material liquid was adjusted by a quantitative pump to a level of 100 g/hr. so that the residence time of the reaction solution became two hours. The flow rate of hydrogen was controlled so that the reaction product will be thereby withdrawn in an amount corresponding to the amount of the feed starting material liquid, and the condensed liquid component and the gas were separated by a condenser outside the system. Upon expiration of 21.5 hours from the initiation of the reaction in such a reaction system, the liquid component and the gas component were collected, and then subjected respectively to gas chromatography analyses. As a result, the conversion of N-methylsuccinic acid imide was 67.7%, the selectivity for N-methylpyrrolidone was 88.2%, and the selectivity for the by-product methane was 3.1%.

EXAMPLE 14

The reaction was conducted in the same manner as in Example 13 except that no phosphoric acid was added into the autoclave, and the reaction pressure was adjusted to 21 kg/cm$^2$G and the retention time was adjusted to 1.7 hours. Upon expiration of 18 hours of the reaction, the condensed liquid and gas were collected and analyzed. As a result, the conversion of N-methylsuccinic acid imide was 66.2%, the selectivity for N-methylpyrrolidone was 83.7%, and the selectivity for by-product methane was 7.3%.

EXAMPLE 15

1.75 g of the same catalyst as used in Example 13, 10 g of N-methylsuccinic acid imide, 40 g of dioxane and 0.0115 g of phosphoric acid were charged into a top and bottom stirring type autoclave having a capacity of 100 ml, and after flushing with hydrogen gas, reacted under a reaction pressure of 50 kg/cm$^2$G at a reaction temperature of 230° C. for 1 hour.

After the completion of the reaction, the reaction solution and gas were collected and analyzed by gas chromatography. As a result, the conversion of N-methylsuccinic acid imide was 63.6%, the selectivity for N-methylpyrrolidone was 92.9%, and the selectivity for by-product gas was 1.64%.

EXAMPLE 16

The reaction was conducted under the same condition as in Example 15 except that no phosphoric acid was added. As a result, conversion of N-methylsuccinic acid imide was 78.6%, the selectivity for N-methylpyrrolidone was 91.7%, and the selectivity for by-product gas was 3.0%.

EXAMPLE 17

The reaction was conducted under the same condition as in Example 15 except that the reaction time was changed to 2 hours. As a result, the conversion of N-methylsuccinic acid imide was 73.8%, the selectivity for N-methylpyrrolidone was 92.6%, and the selectivity for by-product gas was 1.97%.

EXAMPLE 18

1.75 g of a catalyst prepared in accordance with EXAMPLE 13 so that the atomic ratio of Re/Co became 0.1 and the atomic ratio of Mo/Co became 0.015, and 10 g of N-methylsuccinic acid imide, 40 g of 1,4-dioxane and 0.0111 g of concentrated sulfuric acid, were charged into a top and bottom stirring type autoclave having a capacity of 100 ml, and after flushing with hydrogen gas, reacted under a reaction pressure of 50 kg/cm²G at a reaction temperature of 230° C. for 3 hours. After cooling the reaction system, the reaction solution and gas were collected, and analyzed by gas chromatography. As a result, the conversion of N-methylsuccinic acid imide was 71.9%, the selectivity for N-methylpyrrolidone was 92.0%, and the selectivity for by-product gas was 2.42%.

EXAMPLE 19

The reaction was conducted under the same condition as in Example 18 except that no concentrated sulfuric acid was added. As a result of analysis, the conversion of N-methylsuccinic acid imide was 72.7%, the selectivity for N-methylpyrrolidone was 91.6%, and the selectivity for by-product gas was 3.5%.

According to the present invention, in the hydrogenation reduction of a cyclic acid imide or its precursor to obtain the corresponding lactam, high selectivity which has not been possible, can be accomplished, and therefore, its industrial value is significant.

What is claimed is:

1. A method for producing a lactam having the formula:

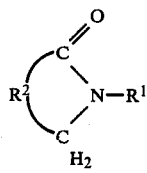
(I)

wherein R¹ is a hydrogen atom, or a straight chain or branched chain alkyl group having from 1 to 5 carbon atoms, and R² is an organic group having at least 2 carbon atoms, and connected at both ends to the cyclic acid imide group, which comprises reducing a cyclic acid imide having the formula:

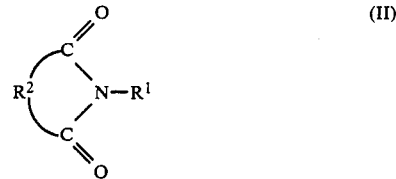
(II)

wherein $R^1$ and $R^2$ are as defined above, or its precursor, with hydrogen by means of a cobalt-based catalyst comprising (a) cobalt and (b) at least one modifier component selected from the group consisting of molybdenum, tungsten and rhenium.

2. The method according to claim 1, wherein the atomic ratio of the modifier component (b) to the cobalt (a) in the catalyst is within a range of from 0.001 to 1.0.

3. The method according to claim 1, wherein the cyclic acid imide is a maleic acid imide or a succinic acid imide.

4. The method according to claim 1, wherein the precursor is a dibasic acid derivative having the formula:

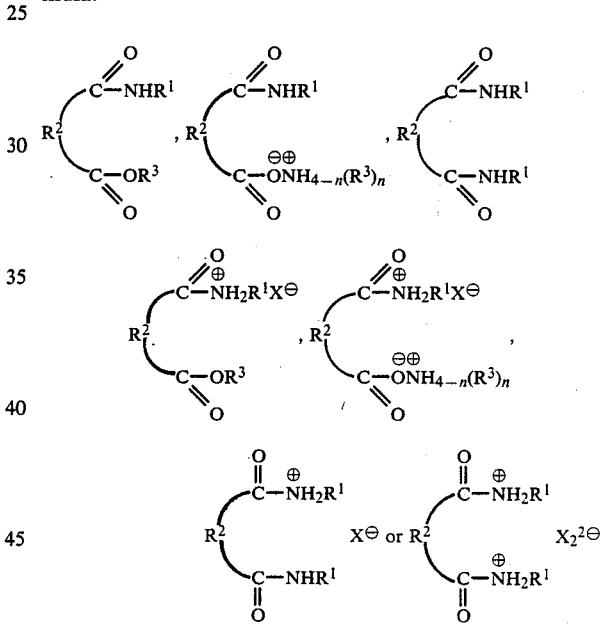

wherein $R^1$ and $R^2$ are as defined in claim 1, $R^3$ is a hydrogen atom, a straight chain or branched chain alkyl group having from 1 to 5 carbon atoms, or an aryl group, X is a mineral acid anion, and n is an integer of from 1 to 3.

5. The method according to claim 1, wherein an acidic substance is added to the reduction reaction system.

6. The method according to claim 5, wherein the acidic substance is a mineral acid, an isopolyacid, a heteropolyphosphoric acid, or a heteropolysilicic acid.

7. The method according to claim 5, wherein the acidic substance is added in an amount of from 10 to 5,000 ppm based on the amount by weight of the liquid in the reaction system.

* * * * *